United States Patent [19]

Arlt

[11] Patent Number: 4,508,913
[45] Date of Patent: Apr. 2, 1985

[54] DIALKOXYMETHYL-BUTYROLACTONES

[75] Inventor: Dieter Arlt, Cologne, Fed. Rep. of Germany

[73] Assignee: Bayer Aktiengesellschaft, Leverkusen, Fed. Rep. of Germany

[21] Appl. No.: 520,676

[22] Filed: Aug. 5, 1983

[30] Foreign Application Priority Data

Aug. 26, 1982 [DE] Fed. Rep. of Germany ....... 3231815

[51] Int. Cl.$^3$ ................... C07D 407/04; C07D 307/32
[52] U.S. Cl. ...................................... 549/320; 549/323; 549/324
[58] Field of Search ................................. 549/320, 323

[56] References Cited

U.S. PATENT DOCUMENTS

| | | | |
|---|---|---|---|
| 3,320,285 | 5/1967 | Martel et al. ......................... | 549/323 |
| 3,758,514 | 9/1973 | Heiba et al. .......................... | 549/320 |
| 4,327,025 | 4/1982 | Jautelat et al. ...................... | 549/320 |
| 4,400,523 | 8/1983 | Jautelat et al. ...................... | 549/320 |

FOREIGN PATENT DOCUMENTS 31932  7/1981  European Pat. Off. .
1128067  4/1962  Fed. Rep. of Germany .

*Primary Examiner*—Norma S. Milestone
*Attorney, Agent, or Firm*—Sprung, Horn, Kramer & Woods

[57] ABSTRACT

The following process steps are shown:

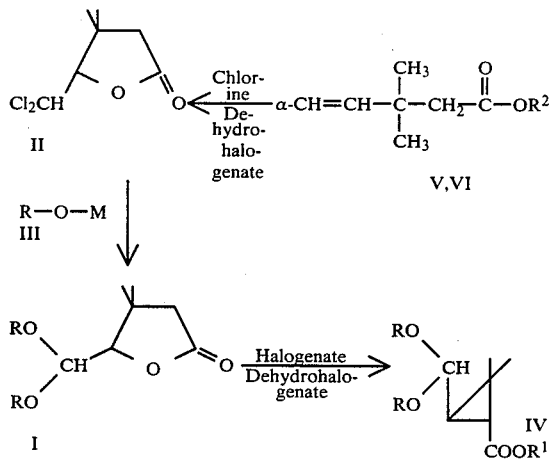

Intermediates I, II, and VI are new. End product IV is a known intermediate in the preparation of known pyrethroid-like cyclopropanecarboxylic acid ester insecticides.

1 Claim, No Drawings

DIALKOXYMETHYL-BUTYROLACTONES

The present invention relates to dialkoxymethyl-butyrolactones, a process for their preparation, new intermediate products for their preparation, and their use for the preparation of caronaldehydic acid derivatives.

Various processes for the preparation of caronaldehydic acids have already been disclosed, for example by partial reduction of cyclopropane dicarboxylic acid half-esters with diborane or sodium borohydride to the hydroxymethyl-cyclopropanecarboxylic acid ester, which is then oxidized with chromic acid in pyridine to give caronaldehydic acid. However, the process is very expensive, since the starting materials used are not readily obtainable (see DE-OS [German Published Specification] No. 2,758,624).

In another process, the starting material is ethyl 4,5-epoxy-3,3-dimethylpentanoate, which is reacted, in absolute aprotic solvents, with lithium diethylamide to give esthyl 2-hydroxymethyl-3,3-dimethyl-cyclopropanecarboxylate, which is then oxidized with chromic acid in pyridine to give caronaldehydic acid. This process, too, uses starting materials which are difficult to obtain and expensive (J. H. Babler et al. J. Org. Chem. 41 page 885 et seq (2976)).

It has furthermore been disclosed (European Patent Application No. 31,932) that caronaldehydic acid derivatives (methyl 2,2-dimethyl-4-formyl-(dimethylacetal)-cyclopropanecarboxylate 9) can be obtained by the reaction route represented below:

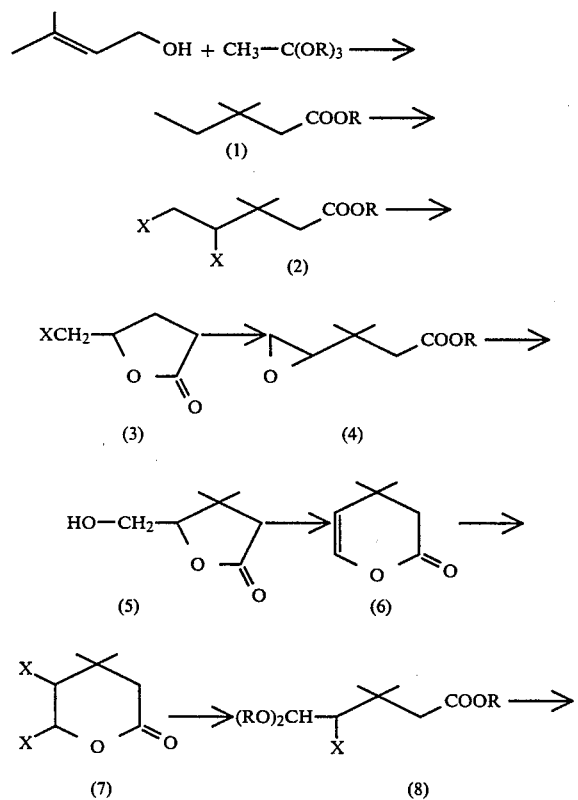

X = Cl or Br    Equation I

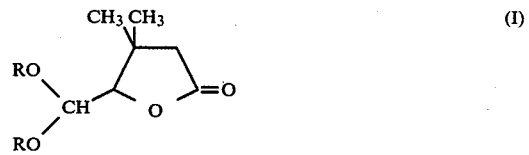

This process, too, has the disadvantage that it uses expensive starting materials. Furthermore, 8 reaction stages are required in order to obtain caronaldehydic acid derivatives (9).

The present application relates to:

1. Dialkoxymethyl-butyrolactones of the formula I

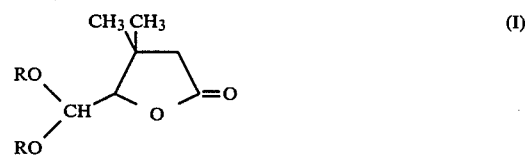

in which
R represents $C_{1-4}$-alkyl, or both radicals R together represent ethylene.

2. Process for the preparation of dialkoxymethyl-butyrolactones of the formula I

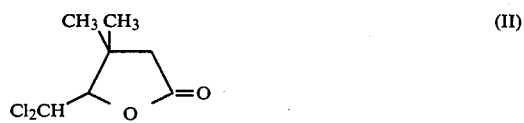

in which
R represents $C_{1-4}$-alkyl, or both radicals R together represent ethylene,
characterized in that dichloromethylbutyrolactones of the formula II

are reacted with alcoholates of the formula III

R—O—M    (III)

in which
R has the meaning given above and
M represents one equivalent of an alkali metal or alkaline earth metal cation.

3. Use of dialkoxymethyl-butyrolactones of the formula I for the preparation of caronaldehydic acid derivatives of the formula IV

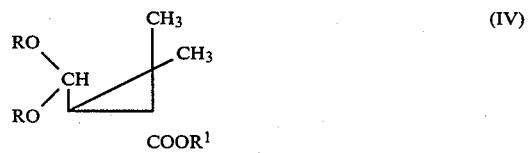

in which

R has the meaning given above and
R$_1$ represents C$_{1-4}$-alkyl,
characterized in that the compound of the formula I is cleaved by halogenation, and the product is dehydrohalogenated, with the formation of a three-membered ring.

4. Dichloromethylbutryolactone of the formula II

5. Process for the preparation of dichloromethylbutyrolactones of the formula II, characterized in that 5-chloro-3,3-dimethyl-pent-4-enoic acid of the formula

or its salts (in particular alkali metal, alkaline earth metal or amine salts), are reacted with chlorine.

6. 5-Chloro-3,3-dimethyl-pent-4-enoic acid (derivatives) of the formula VI

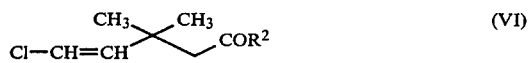

in which
R$^2$ represents OH, C$_{1-4}$-alkoxy or halogen.

7. Process for the preparation of 5-chloro-3,3-dimethyl-pent-4-enoic acid (derivatives) of the formula VI, characterized in that 5,5-dichloro-3,3-dimethylpentanoic acid esters of the formula VII

in which
R$^1$ represents C$_{1-4}$-alkyl,
are reacted with bases, and the resulting esters of 5-chloro-3,3-dimethyl-pent-4-enoic acid are then derivatized in a customary manner.

With the aid of the new compounds and the processes for their preparation, a new economical process for the preparation of caronaldehydic acid esters has been found. This new process has the advantage that it uses simple and cheap starting materials. Thus, 1,1,5,5-tetrachloro-3,3-dimethyl-pent-1-ene, from which 5,5-dichloro-3,3-dimethylpentanoic acid of the formula VII is obtained, is obtainable in very good yields from carbon tetrachloride, iso-butene and vinyl chloride, via two stages. Further reaction to give the caronaldehydic acid ester takes place in 5 stages. That is to say, compared with the process known from the prior art, one stage less is required.

It was surprising that the entire process for the preparation of caronaldehydic acid esters could be carried out with the aid of the new compounds. The advantage of the new process is that cheaper starting materials can be used, and that, altogether, one reaction stage less is required in order to obtain the caronaldehydic acid ester.

The course of the overall reaction was surprising not only because in order to carry it out new compounds had to be employed, about the properties and reactivities of which nothing was known hitherto; it was also surprising that the courses of the various reaction steps carried out were at all as described.

Thus, it was not to be expected that the process under 5 (above) would proceed smoothly and with good yields. It was to have been expected that, as a result of halogen addition at the double bond and as a result of the formation of a 6-membered cyclic lactone instead of the desired butyrolactone, the yield and purity of the compound of the formula II would be so poor that the overall process could not be carried out economically.

Thus, it was also not to be expected that the process under 2 (above) would proceed smoothly and with good yields. In this case, too, side-reactions (HCl elimination to yield a double bond) were to be expected, and the yield and purity could have made the process uneconomical.

The dialkoxymethyl-butyrolactones of the formula I are new. In formula I, R preferably represents methyl or ethyl. They are prepared by the process given under 2 (above). If dichloromethylbutyrolactone and sodium methylate are used, this process can be represented by the following equation:

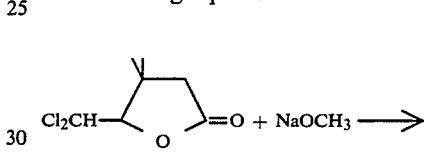

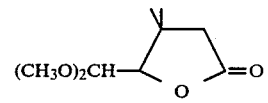

The reaction is carried out at between 20° and 100° C., preferably between 20° and 80° C. The reaction is carried out in general under atmospheric pressure. The reaction is carried out in inert solvents. Preferred solvents are the alcohols from which the alcoholates are derived, that is to say, for example, methanol.

The compounds of the formula I can be isolated from the reaction mixture in a customary manner by distillation. However, they can also be directly reacted further, in the form of the reaction mixture, without isolation, to give the compounds of the formula IV. For this purpose, hydrogen chloride is passed into the reaction mixture obtained in the formation of the compounds of the formula I, and after the reaction is complete, alkali metal alcoholates, such as sodium methylate or sodium ethylate, are added to the mixture.

Compounds of the formula IV are also obtained when butyrolactones of the formula I are reacted with thionyl chloride or phosphorus pentachloride, for example at temperatures between 0° and 40° C., and the product obtained is treated with alcohols and basic agents. Examples of suitable alcohols are methanol and ethanol, and examples of suitable basic agents are Na methylate and ethylate or DBU or DBN.

The butyrolactones of the formula I are isolated in a manner which is in itself known, for example by distillation.

Dichloromethyl-butyrolactone of the formula II is new. It is obtained according to the following equation:

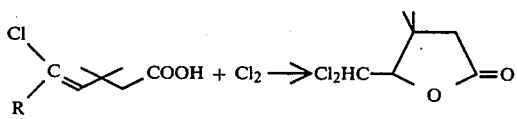

The reaction is carried out by reacting the acid of the formula V, or salts of this acid, with chlorine to give 5-dichloromethyl-4,4-dimethyl-butyrolactone of the formula II. The reaction is carried out at temperatures between about −20° and 50° C., in inert solvents, such as, for example, dichloromethane or trichloromethane. Suitable salts are the alkali metal salts of the acid of the formula V, but its salts with tertiary bases, such as, for example, trimethylamine or triethylamine, can also be used. The lactone of the formula II can be isolated in pure form by fractional distillation, if appropriate after the resulting salts, for example triethylammonium chloride, or the hydrogen chloride formed have been extracted beforehand from the reaction mixture with water.

5-Chloro-3,3-dimethyl-pent-4-enoic acid and its derivatives of the formula V and VI are new.

They are obtained according to the following equation:

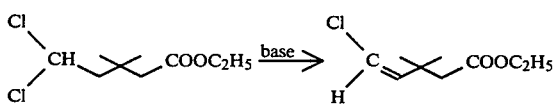

The acid of the formula V, or its salts, are obtained by customary hydrolysis of the ester.

The ester of 5,5-dichloro-3,3-dimethyl-pentanoic acid is dehydrohalogenated by the action of bases, esters of 5-chloro-3,3-dimethyl-pent-4-enoic acid of the formula V being obtained. Examples of dehydrohalogenating agents which are used are alcoholates, such as Na methylate, Na ethylate and Na butylate, and tertiary bases, such as triethylamine, N,N-dimethylbenzylamine, DBU and DBN. The dehydrohalogenation is carried out in general at temperatures between 65° C. and 150° C., and the solvents used are, for example, alcohols, such as methanol, ethanol and butanol, or aprotic solvents, such as dimethylformamide and diethylene glycol dimethyl ether. The ester obtained can be isolated in pure form, for example by distillation. However, it can also be hydrolyzed in situ by reaction with alkalis. Examples of alkalis used are sodium hydroxide and potassium hydroxide. This ester hydrolysis is carried out, for example, in alcohols at temperatures between 20° and 80° C. The 4-chloro-3,3-dimethyl-pent-4-enoic acid is then liberated by acidification with mineral acids, such as hydrochloric acid or sulphuric acid, and is obtained in pure form, for example by distillation.

It is also possible to obtain the chloride of the acid of the formula V from 5,5-dichloro-3,3-dimethylpentanoic acid-chloride by catalytic dehydrohalogenation. Suitable catalysts are, for example, active charcoal doped with metal salts, it being possible to use, for example, BaCl$_2$, FeCl$_3$, ZnCl$_2$ and CuCl as salts. The dehydrohalogenation, which can be effected both in the liquid phase and in the gas phase, is carried out at temperatures between 150° and 300° C. The resulting acid-chloride of the acid of the formula V is purified by distillation. It can be hydrolyzed to the acid of the formula V in a manner which is in itself known.

5,5-Dichloro-3,3-dimethylpentanoic acid of the formula VII and its preparation are taught in Application Ser. No. 518,855, filed Aug. 1, 1983, now pending (corresponding to German Application No. P 32 30 274.6, filed Aug. 14, 1982—Le A 21 874).

They are obtained by acid hydrolysis of 1,1,5,5-tetrachloro-3,3-dimethyl-pent-1-ene, for example with sulphuric acid. During the hydrolysis, a temperature range of about 20°–100° C., preferably 40°–70° C., is maintained. In general, an excess of acid is employed, but the reaction mixture should at least contain an amount of water equivalent to the pentene employed. In addition to sulphuric acid, other strong acids, such as, for example, phosphoric acid, methanesulphonic acid, trifluoroacetic acid and mixtures of formic acid and hydrochloric acid, are also suitable for the hydrolysis.

If it is desired to isolate the acid of the formula VII, the reaction mixture is diluted with water, and the acid of the formula VII is extracted with solvents, such as, for example, chlorohydrocarbons. When distillable acid mixtures are used, such as, for example, the reaction mixtures obtained after the hydrolysis with trifluoroacetic acid or formic acid/hydrochloric acid, the mixture is worked up by distillation in order to obtain the acid of the formula VII in pure form.

However, it is also possible for the reaction mixtures obtained after the acid hydrolysis to be directly reacted further (see process 7).

In order to obtain 5-chloro-3,3-dimethyl-pent-4-enoic acid of the formula V, the compound of the formula VII is first converted to an ester. This can be effected, for example, in a known manner, by reaction with thionyl chloride or phosgene to give the 5,5-dichloro-3,3-dimethylpentanoic acid-chloride and subsequent reaction of this compound with alcohols, such as, for example, methanol or ethanol. It is also possible to react the acid directly with alcohols in the presence of known esterification catalysts, it being advantageous to remove the resulting water of reaction by azeotropic distillation. For the preparation of the ester of the acid of the formula VII, it is particularly advantageous if the reaction mixtures obtained from 1,1,5,5-tetrachloro-3,3-dimethyl-pent-1-ene are reacted with alcohols. In this case, the ester formed is isolated, for example, by extraction with solvents, such as, for example, hexane, if appropriate after dilution of the reaction mixture with water, and is purified by distillation.

1,1,5,5-Tetrachloro-3,3-dimethyl-pent-1-ene is known. It is obtainable economically from carbon tetrachloride, iso-butene and vinyl chloride by processes which are in themselves known.

EXAMPLE 1

5,5-Dichloro-3,3-dimethyl-pentanoic acid 500 g of 1,1,5,5-tetrachloro-3,3-dimethyl-pentene are metered into 2400 ml sulphuric acid (96%) while stirring, in the course of 1 hour at a rate such that the reaction mixture does not exceed 45° C. The reaction mixture is kept at 40°–45° C. for a further 24 hours and then introduced onto 4 kg of ice. The mixture is extracted several times with dichloromethane. After the solvent has been distilled off, 420 g of crude 5,5-dichloro-3,3-dimethyl-pentanoic acid are obtained, and after distillation 380 g of pure 5,5-dichloro-3,3-dimethylpentanoic acid of boiling point 103°–106° C./0.2 are obtained.

EXAMPLE 2

5,5-Dichloro-3,3-dimethyl-pentanoic acid-chloride 52.25 g of 5,5-dichloro-3,3-dimethyl-pentanoic acid are reacted with 150 ml of thionyl chloride, first at room temperature and thereafter while warming at 60° C. By working up the mixture by distillation, 56.5 g of 5,5-dichloro-3,3-dimethyl-pentanoic acid-chloride of boiling point 114°–115° C./15 are obtained.

EXAMPLE 3

Methyl 5,5-dichloro-3,3-dimethyl-pentanoate 22.5 g of the acid-chloride obtained according to Example 2 are added dropwise to 100 ml of methanol, and the mixture is then warmed for 1 hour to 65° C. By distillation of the reaction mixture, 20.5 g of methyl 5,5-dichloro-3,3-dimethyl-pentanoate of boiling point 110°–112° C./15 are obtained.

EXAMPLE 4

Methyl 5-chloro-3,3-dimethyl-pent-4-enoate 62.8 g of the ester obtained according to Example 3 and 40.5 g of DBN (diazabicyclononane) in 250 ml of dimethoxyethane are warmed at the reflux temperature for 40 hours.

Thereafter, the solvent is distilled off and 250 ml of dichloromethane are added to the residue, and the mixture is extracted with dilute hydrochloric acid. By distillation of the organic phase, 30 g of methyl 5-chloro-3,3-dimethyl-pent-4-enoate of boiling point 87°–88° C./12 are obtained.

EXAMPLE 5

5-Chloro-3,3-dimethyl-pent-4-enoic acid-chloride 38 g of the ester obtained according to Example 4 are warmed at 40° C. for 8 hours with 13 g of KOH, dissolved in 120 ml of methanol. Thereafter, the methanol is distilled off and the residue is taken up with 150 ml of water, and the mixture acidified with hydrochloric acid. The mixture is then extracted with dichloromethane, and the solvent is evaporated in vacuo. 100 ml of thionyl chloride are added to the acid which remains, and the mixture is warmed at 60° C. for 4 hours. After the reaction mixture has been distilled, 36 g of 5-chloro-3,3-dimethyl-pent-4-enoic acid-chloride of boiling point 86°–90° C./15 are obtained.

EXAMPLE 6

4-Dichloromethyl-3,3-dimethyl-butyrolactone 13.1 g of the acid-chloride obtained according to Example 5 are added dropwise to a stirred mixture of 4 g of water in 150 ml of dichloromethane. The mixture is heated at the reflux temperature for 8 hours. Thereafter, the solvent, residual water and hydrogen chloride are removed in vacuo. The residue (5-chloro-3,3-dimethyl-pent-4-enoic acid) is dissolved in 50 ml of dichloromethane.

9.2 g of triethylamine are added to this solution, and approximately 7 g of chlorine are then passed into this salt solution, while cooling at 0° C.

In order to isolate the 4-dichloromethyl-3,3-dimethyl-butyrolactone formed, the solution obtained is extracted with water, and the organic phase is dried (Na$_2$SO$_4$) and distilled. 8.5 g of 4-dichloromethyl-3,3-dimethyl-butyrolactone of boiling point 88°–92° C./0.15 are obtained.

Advantageously, the crude reaction product obtained is reacted further in solution, according to Example 7.

EXAMPLE 7

The solution of 4-dichloromethyl-3,3-dimethyl-butyrolactone in dichloromethane, obtained according to Example 6, is added dropwise to a solution of 6.5 g of Na in 100 ml of absolute ethanol at 0° C. Thereafter, the mixture is warmed to the reflux temperature and the dichloromethane is distilled off over a column. After 6 hours, ice-water is added to the reaction solution, and the mixture is extracted several times with dichloromethane. Fractional distillation of the dichloromethane solution gives 8.9 g of 4-diethoxymethyl-3,3-dimethyl-butyrolactone of boiling point 78°–80° C./0.08.

EXAMPLE 8

8.9 g of the 4-diethoxymethyl-3,3-dimethyl-butyrolactone obtained according to Example 7 are dissolved in 80 ml of absolute ethanol, and hydrogen chloride is passed into the solution at room temperature. After 10 hours, the solvent and excess hydrogen chloride are evaporated in vacuo. The residue is added dropwise to a solution of 1 g of Na in 100 ml of methanol, and the mixture is warmed at 75° C. for 5 hours. After filtration of the precipitated sodium chloride, the reaction mixture is distilled. 5 g of caronaldehydic acid ethyl ester diethyl acetale of boiling point 73° C.–77° C./0.04 are obtained.

It is understood that the specification and examples are illustrative but not limitative of the present invention and that other embodiments within the spirit and scope of the invention will suggest themselves to those skilled in the art.

I claim:

1. A dialkoxymethyl-butyrolactone of the formula

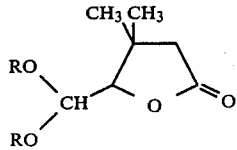

in which

R is C$_{1-4}$-alkyl, or both radicals R together are ethylene.

* * * * *